(12) United States Patent
Detournay et al.

(10) Patent No.: US 9,156,866 B1
(45) Date of Patent: Oct. 13, 2015

(54) METHODS FOR RECOVERING BIS(2,4,4-TRIMETHYLPENTYL) DITHIOPHOSPHINIC ACID

(71) Applicant: VALE S.A., Rio de Janeiro (BR)

(72) Inventors: Marc Detournay, Nouméa (NC); Arnaud Jacques De Sainte Marie, Nouméa (NC); Jean-Paul Raymond Duterque, Nouméa (NC); Indje Ognianov Mihaylov, Mississauga (CA)

(73) Assignee: VALE S.A., Rio de Janeiro (BR)

( * ) Notice: Subject to any disclaimer, the term of this patent is extended or adjusted under 35 U.S.C. 154(b) by 0 days.

(21) Appl. No.: 14/482,972

(22) Filed: Sep. 10, 2014

(51) Int. Cl.
*C07F 9/30* (2006.01)

(52) U.S. Cl.
CPC ...................................... *C07F 9/301* (2013.01)

(58) Field of Classification Search
None
See application file for complete search history.

(56) References Cited

U.S. PATENT DOCUMENTS

| 5,378,262 A | 1/1995 | Mihaylov et al. |
| 5,759,512 A | 6/1998 | Rickelton et al. |
| 6,022,991 A | 2/2000 | Perraud et al. |

FOREIGN PATENT DOCUMENTS

EP 0 210 387 A1 2/1987

OTHER PUBLICATIONS

Zhu, et al., Solvent Extraction and Ion Exchange, 14(1), 61-68 (1996).*
Chen, et al., "A Study on the Radiolytic Stability of Commercial and Purified Cyanex 301," Solvent Extraction and Ion Exchange, 14(4), 555-565 (1996).
Chen, et al., "The Separation of Am from Lanthanides by Purified Cyanex 301 Extraction," Separation Science and Technology, 31(19), pp. 2723-2731, 1996.
Cyanex® 301 Extractant—Technical brochure, Cytec, pp. 1-14.
Groenewold, et al, "Oxidative degradation of bis(2,4,4-trimethylpentyl)dithiophosphinic acid in nitric acid studied by electrospray ionization mass spectrometry," Rapid Commun. Mass Spectrom. 2012, 26, 2195-2203.
Zhu, et al., "Extraction of Am(III) and Eu(III) from Nitrate Solution with Purified Cyanex 301," Solvent Extraction and Ion Exchange, 14(1), 61-68 (1996).

* cited by examiner

*Primary Examiner* — Karl J Puttlitz
(74) *Attorney, Agent, or Firm* — Arent Fox LLP

(57) ABSTRACT

This invention provides a method to recover valuable DTPA from DTPA solvent extraction organic solution that avoids the need to operate at either high or very low temperatures, with extended reaction times and having to carry out solid/liquid separation on organic solution. Furthermore, the invention provides the flexibility of selecting appropriate base solution to carry out the DTPA recovery process and further provides the ability to directly treat metal-containing DTPA organic solution.

21 Claims, 3 Drawing Sheets

METHODS FOR RECOVERING BIS(2,4,4-TRIMETHYLPENTYL) DITHIOPHOSPHINIC ACID

FIELD OF THE INVENTION

The proposed invention refers to a method for recovering DTPA bis(2,4,4-trimethylpentyl)dithiophosphinic acid from other organophosphorus impurities while avoiding the need to operate at extreme temperatures or producing, and having to deal with, organic solids.

BACKGROUND OF THE INVENTION

Hydrometallurgical processing of lateritic ores for nickel and cobalt recovery, based on high-pressure sulfuric acid leaching (HPAL), has been gaining technological and commercial acceptance over the last 20 years.

Once nickel and cobalt values are transferred from the laterite ore into the sulfuric acid leach solution in the HPAL autoclave, a number of different refining routes have been developed for recovering the nickel and cobalt from the leach solution into saleable products. Solvent extraction (SX), employing metal extractants dissolved in suitable hydrocarbon diluents, is often used in one or more steps within these refining routes.

One of the extractants used in the hydrometallurgical processing of lateritic ores for nickel and cobalt recovery is Cyanex 301, a solvent extractant developed by Cytec Industries (EP 021387). The use of Cyanex 301 allows for the selective transfer of nickel and cobalt from the sulfate leach solution into an upgraded hydrochloric acid leach solution, from which nickel and cobalt are separated and refined to final products (U.S. Pat. No. 5,378,262).

Bis(2,4,4-trimethylpentyl)dithiophosphinic acid (referred hereto as dithiophosphinic Acid or DTPA) is the active ingredient of the Cyanex 301. Being an organic thiol ($[C_8H_{17}]_2P(S)SH$), DTPA can undergo oxidation. A common oxidation path generates disulfide:

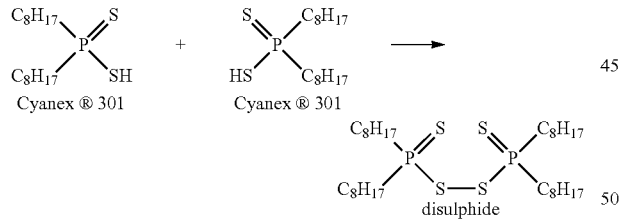

The disulfide can be regenerated back to DTPA and Vale has developed regeneration processes to achieve that (U.S. Pat. No. 5,759,512 and U.S. Pat. No. 6,022,991). These regeneration processes support the commercial viability of using Cyanex 301 for metal extraction.

The oxidation of DTPA can result in the formation, over time, of oxidation products other than disulfide. These oxidation products can be generally described as organophosphorus compounds that contain sulfur and/or oxygen. These compounds do not have the extractive and metal selectivity properties of DTPA and cannot be readily reduced back to DTPA. Hence, as Cyanex 301 (DTPA) is added in order to maintain the metallurgy-required DTPA concentration in the organic solution, these compounds will accumulate over time.

Their presence in the organic solution can be followed by suitable methods of analysis, including phosphorus nuclear magnetic resonance ($^{31}$P-NMR), chemical analysis for phosphorus and sulfur as well as acid titration determination for acids such as DTPA.

The accumulation of these compounds in the SX organic solution can impact the desirable metallurgy of the Cyanex 301 based SX system by impacting the physical properties of the organic solution, such as viscosity, interfacial tension and the like and/or by affecting the ability of the extractant system to maintain the desired degree of metal extraction selectivity.

Thus, removal for some of the SX organic solution (organic bleed) from the operating organic circuit becomes necessary. The obvious disadvantage of this approach is the loss of DTPA with the organic bleed. Furthermore, disposal of the organic bleed itself will add further costs.

Therefore, a process that would enable the recovery of DTPA from the organic bleed and its separation from the accumulating oxidation products would be metallurgically and operationally advantageous as well as economically desirable.

Given that the DTPA content of Cyanex 301 is about 75-80% [Cyanex® 301 Extractant—Technical brochure, Cytec] and that it also contains other organothiophosphorus compounds, a purification technique was developed by Zhu et al [Zhu, Y., Chen, J., Jiao R., 1996, Extraction of Am(III) and Eu(III) from Nitrate Solution with Purified Cyanex 301, *Solvent Extraction and Ion Exchange*, 14(1), 61-68] aimed at isolating high purity DTPA, primarily for the purpose of fundamental metal extraction chemistry research.

In the Zhu purification technique, Cyanex 301 is contacted with ammonium carbonate solution at 70° C. for one hour to produce the ammonium salt of DTPA (ammonium dithiophosphinate) and then the mixture is left overnight at 0° C. to allow for the crystallization of the ammonium salt; the crystalized solids are eventually converted back to DTPA by contact with 4 N hydrochloric acid. This purification technique has been subsequently used by other researchers, e.g., [Groenewold, G. S, Peterman, P. R., Klaehn, J. R., Delmau, L. H., Marc P., Custelcean, R., 2012, *Oxidative degradation of bis(2,4,4-trimethylpentyl)dithiophosphinic acid in nitric acid studied by electrospray ionization mass spectrometry*, Rapid Commun. Mass Spectrom., 26, 2195-2203.] for similar purposes.

Applying this technique on an industrial scale will be very difficult and costly for the following reasons:
- use of elevated temperatures and prolonged time for the contact with the ammonium carbonate solution, which could result in further oxidation of DTPA;
- need to cool the mixture to 0° C. for a long period of time in order to produce the ammonium dithiophosphinate solids; and
- need to carry out filtration of the ammonium dithiophosphinate solids from the organic solution, while likely having to maintain temperatures near 0° C.

Therefore, there is a need for a method that will be able to effectively separate DTPA from other organophosphorus impurities while avoiding having to operate at extreme temperatures or producing, and having to deal with, organic solids.

It has now been discovered that DTPA can be effectively and efficiently recovered from DTPA-containing organic solutions and various other organophosphorus compounds, as described earlier, in which solutions DTPA is present in its acid form and/or in its base metals-salt form, where the group of base metals include nickel, cobalt, zinc, copper, chromium and the like, without the formation of solids or the necessity of maintaining low temperatures over long period of time.

The method avoids the need for elevated temperatures (above 70° C.), the need for operating at very low (near 0° C.) temperatures, the prolonged reaction times and the generation and handling of organic solids.

This is accomplished by contacting the DTPA-containing organic solution with a suitable aqueous base solution supplied in excess of the stoichiometric requirement for the acid-base neutralization or other metal cation-exchange reactions for the contained DTPA. This prevents the formation of solids that would otherwise form from the treated DTPA-containing solution.

SUMMARY OF THE INVENTION

Figure 1:
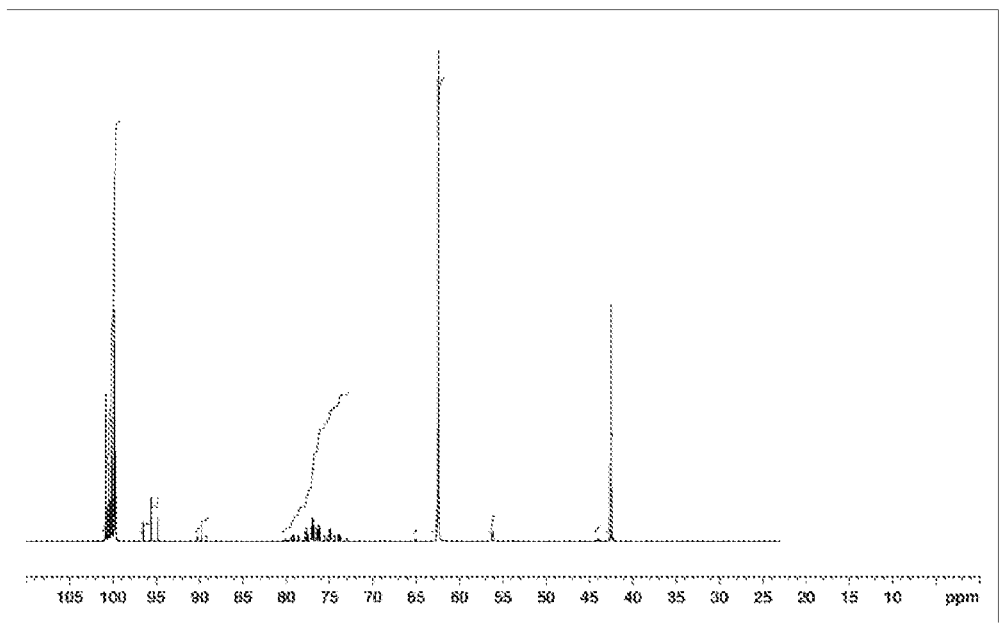
FIG. 1 shows a typical $^{31}$P-NMR spectrum of field organic solution.
Figure 2:
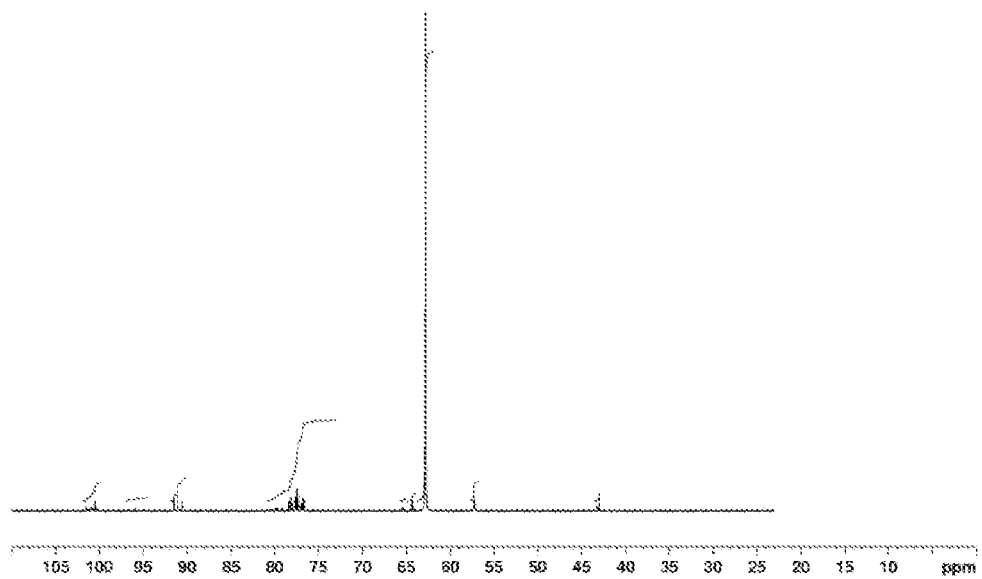
FIG. 2 shows a typical $^{31}$P-NMR spectrum of DTPA-recovered product organic solution.
Figure 3:
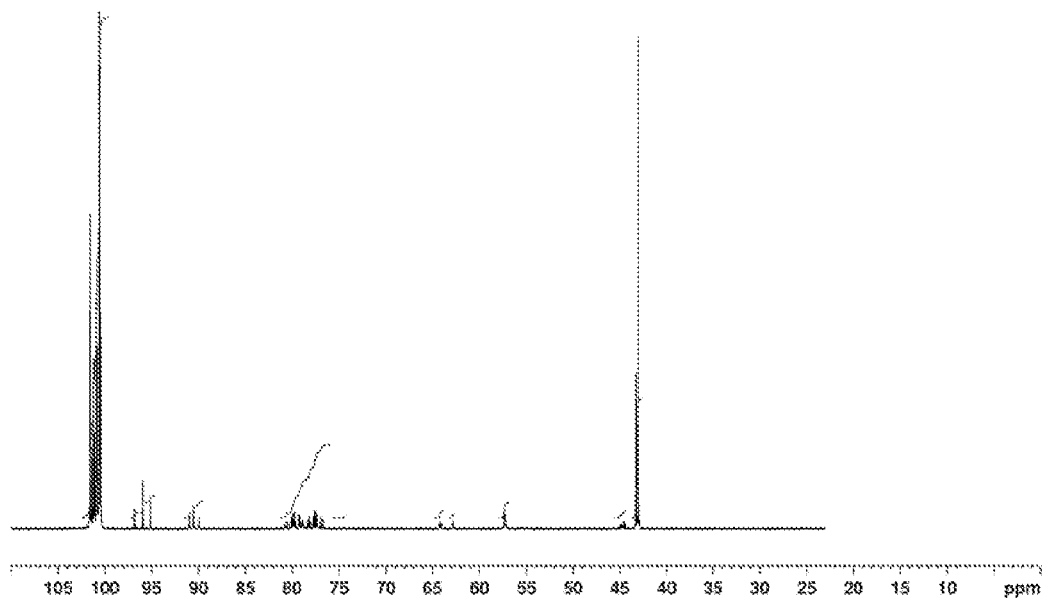
FIG. 3 shows a typical $^{31}$P-NMR spectrum of light (DTPA-lean) organic solution.

The present invention refers to a method for recovering bis(2,4,4-trimethylpentyl)dithiophosphinic acid (DTPA) from organic solution containing DTPA and various other organophosphorus compounds that have been generally produced from the oxidation of DTPA and are different from disulfide and may also contain base metals, such as nickel, cobalt, zinc, copper and chromium, chemically bonded to DTPA, comprising the following steps: (a) contacting the DTPA-containing solution with a suitable aqueous base solution supplied in excess of the stoichiometric requirement for the acid-base neutralization or other metal cation-exchange reactions for the contained DTPA to produce a DTPA-rich and a DTPA-lean organic phases; (b) separation the two organic phases; (c) contacting the DTPA-rich organic phase with suitable acidic solution to produce a base-free DTPA-rich organic solution; and (d) contacting the DTPA-lean organic phase with suitable acidic solution to produce a base-free DTPA-lean organic solution.

DETAILED DESCRIPTION OF THE INVENTION

The present invention overcomes the drawbacks of the prior art by providing a method to recover DTPA from DTPA-containing organic solution and various other organophosphorus compounds that have been generally produced from the oxidation of DTPA and are different from disulfide and may also contain base metals, such as nickel, cobalt, zinc, copper and chromium, chemically bonded to DTPA.

The method comprises the following steps: (a) contact of the DTPA-containing solution with a suitable aqueous base solution supplied in excess of the stoichiometric requirement for the acid-base neutralization or other metal cation-exchange reactions for the contained DTPA to produce a DTPA-rich and a DTPA-lean organic phases; (b) separation of the two organic phases; (c) contact of the DTPA-rich organic phase with suitable acidic solution to produce a base-free DTPA-rich organic solution; and (d) contact of the DTPA-lean organic phase with suitable acidic solution to produce a base-free DTPA-lean organic solution.

The treatment of step (a) is carried out at moderate temperatures within the range between 25 and 70° C., more preferably at temperatures between 35 and 60° C. and most preferably at temperatures between 45 and 55° C.

Suitable aqueous base solutions for step (a) include aqueous solutions of alkali-metals hydroxides, such as sodium hydroxide and potassium hydroxide, ammonium hydroxide and the like. More advantageously, the base is selected from the group of sodium hydroxide and ammonium hydroxide. Most advantageously, the base is ammonium hydroxide solution.

The base solutions can be used over a range of concentrations, preferably greater than 1 mol/L. More advantageously, the base solutions with concentration greater than 5 mol/L are used. Most advantageously, a 50 wt % sodium hydroxide or a 28 wt % ammonia solution is used.

In the present invention, the organic solution of Cyanex 301, dissolved in suitable hydrocarbon diluent, which contains DTPA together with various other organophosphorus compounds that have been generally produced from the oxidation of DTPA (further referred to as 'field organic'), and may also contain base metals, such as nickel, cobalt, zinc, copper and chromium, chemically bonded to DTPA, is contacted with suitable aqueous base such solution as alkali-metal hydroxide or ammonium hydroxide, added in excess of the stoichiometric equivalent for the amount of DTPA present in the organic solution in an acid- and or metal-bonded form.

This contact, carried out in a suitable mixing vessel and at moderate temperatures, produces a solids-free mixture of at least two distinct solutions (DTPA-rich organic phase and DTPA-lean organic phase) that can be readily separated (step b).

The separation in step (b) can be carried out by a variety of means, based on the different specific densities of the distinct solutions formed; these means include separation by gravity, separation by centrifuging and the like.

The heavier solution is the DTPA-rich organic phase which contains DTPA and its respective base salt, such as sodium, potassium or ammonium dithiophosphinate.

The lighter solution is the DTPA-lean organic phase which comprises the hydrocarbon diluent containing the majority of the organophosphorus compounds that have been generally produced from the oxidation of DTPA.

Depending on the particular conditions, such as the concentration of base solution and/or its addition dosage, a third phase, comprising an aqueous base solution, may be formed as well.

Following the separation, the recovered DTPA-rich organic solution obtained in step (c) is suitable for re-use for metal extraction operation.

Depending on the particular operating circumstances, it may be advantageous, to contact the DTPA-rich organic solution obtained in step (c) with a suitable acid aqueous solution in order to convert the base salt form of DTPA, such as sodium, potassium or ammonium dithiophosphinate, into the acid form of DTPA and/or dilute the DTPA-rich organic solution obtained in step (c) to lower the DTPA concentration by using, for example, DTPA-containing organic solution from the solvent extraction operation or organic diluent used when preparing that organic solution. In this way the properties of the DTPA-rich solution, such as its specific gravity and viscosity, in addition to the DTPA concentration, can be suitably brought closer to those of the organic solution present in the solvent extraction circuit operation such that to avoid wide operational swings in the properties of the solvent extraction organic solution.

A variety of suitable acid aqueous solutions can be used to convert the base salt form of DTPA into the acid form of DTPA. Advantageously, the acid aqueous solutions contain at least one mineral acid. More advantageously, the mineral acid is selected from the group of hydrochloric and sulfuric acid. Most advantageously the mineral acid is sulfuric acid.

The DTPA-lean organic phase comprising the hydrocarbon diluent and the majority of the organophosphorus compounds that have been generally produced from the oxidation of DTPA, can be further treated by a variety of known means, such as solvent distillation, steam stripping and the like, to separate and recover the majority of the hydrocarbon diluent from the higher boiling point organophosphorus compounds.

This allows for the majority of the hydrocarbon diluent to be recovered and returned into the solvent extraction operation while greatly reducing the volume of the remaining organic solution, now containing in much more concentrated form the organophosphorus compounds that have been generally produced from the oxidation of DTPA, for disposal.

The present invention is illustrated by the following examples:

Example 1

A 200 mL sample of nickel-free field organic Cyanex 301 solution, having a specific gravity of 0.81 and analyzing 0.211 mol/kg (0.171 mol/L) DTPA, 19.0 g/kg P, 33.1 g/kg S, is mixed with 12 grams of 50 wt % NaOH solution (6 g of NaOH) at 65° C. for 20 minutes. A heavier organic phase is formed and then separated by gravity.

Analysis of this organic phase shows that it contained 1.31 mol/kg DTPA, 38.5 g/kg P and 90.3 g/kg S.

Considering that each mole of DTPA represents one mole of P and two moles of S, it is readily evident that the DTPA (0.211 mol/kg) in the field organic accounts only for 6.54 g/kg P and 13.5 g/kg S, representing about 34% of the total P (19.0 g/kg) and 41% of the total S (33.1 g/kg) content of the field organic. In contrast, in the recovered organic phase, the 1.31 mol/kg DTPA represents 105% of the total P (40.6 g/kg P equivalent to DTPA) and 93% of the total S (83.8 g/kg S equivalent to DTPA).

Example 2

A 200 mL sample of the same nickel-free field organic Cyanex 301 solution, as described in Example 1, is mixed with 24.3 grams of 28 wt % ammonia solution (6.8 g of $NH_3$) and under the same conditions. Formation of solids was observed and the recovered DTPA-rich organic phase contained 0.86 mol/kg DTPA, 35.3 g/kg P and 67.4 g/kg S. From the analysis of this phase, it is evident that the DTPA separation from other organophosphorus species was inferior to what was achieved in Example 1: the 0.86 mol/kg DTPA accounts for 76% of the total P (26.7 g/kg P equivalent to DTPA) and 82% of the total S (55.0 g/kg S equivalent to DTPA).

The ammonia dosage (6.8 g of $NH_3$ equivalent to 0.4 moles of $NH_3$) compared to the 0.034 moles of DTPA in the sample (200 mL of 0.171 mol/L DTPA) represents ~12 times the stoichiometric requirement for acid-base neutralization.

Example 3

The test described in Example 2 was repeated under otherwise the same conditions but with a higher dosage of the base solution, 40.7 grams of the same 28 wt % ammonia solution (11.4 g of $NH_3$), only the heavier, DTPA-rich organic phase was formed. There was no formation of solids observed. The recovered DTPA-rich organic phase contained 1.66 mol/kg DTPA, 40.7 g/kg P and 79.9 g/kg S, indicating the essentially complete removal of the non-DTPA organophosphorus compounds.

The ammonia dosage (11.4 g of $NH_3$ equivalent to 0.67 moles of $NH_3$) compared to the 0.034 moles of DTPA in the sample (200 mL of 0.171 mol/L DTPA) represents ~20 times the stoichiometric requirement for acid-base neutralization.

This example illustrates the importance of base dosage for preventing solids formation as well as achieving the high degree of DTPA separation.

Example 4

The test described in Example 1 was repeated under otherwise the same conditions but using a field organic solution containing chemically extracted nickel at several gram per liter concentration.

Even with a higher dosage of 50 wt % NaOH solution, a precipitate of nickel hydroxide intermixed with an organic phase was produced. Effective physical separation of such mixture of fine solid precipitate and organic solution will be challenging.

This example illustrates that while sodium hydroxide is effective for DTPA recovery, its application would be restricted to nickel-free DTPA containing organic solution.

Example 5

One liter samples of field organic solution, containing different amounts of nickel, were each contacted for 5 minutes with 220 mL of 28 wt % ammonia solution, at 55° C.

In every case, three distinct phases were formed and allowed to separate. There was no formation of nickel precipitate solids; it is known from prior art that nickel remains soluble in ammoniacal solutions due to the formation of aqueous soluble nickel amine complexes.

The lighter organic phase was collected and then contacted with 6 N HCl solution to remove residual ammonia. Similarly, the heavier DTPA-rich organic phase was separated and then also contacted with 6 N HCl solution to remove residual ammonia. The residual third phase, representing unreacted ammonia aqueous solution was removed.

The organic phases from all three tests were sampled for DTPA and chemical analysis as well as $^{31}P$-NMR analysis. The results are summarized in the table below.

The $^{31}P$-NMR analysis confirms the high degree of separation for DTPA from the other organophosphorus species, indicated through the DTPA acid titration and organic chemical analyses. The overall DTPA recovery to the heavier organic phase is in the 90% range.

| | Field Organic I | Field Organic II | Field Organic III |
|---|---|---|---|
| DTPA in the field sample (mol/L) | 0.174 | 0.197 | 0.217 |
| Nickel in the field sample (g/L) | 2.6 | ~5.7-6.0 | |
| DTPA in the recovered product organic (mol/L) | 1.646 | 1.584 | 1.554 |
| % of P with DTPA as % of total P in field sample | 32% | 34% | 43% |
| % of P with DTPA as % of total P in product sample | 83% | 86% | 85% |
| DTPA in field sample as % of all organophosphorus compounds (from $^{31}P$-NMR) | 27 | 32 | 39 |
| DTPA in the light organic sample as % of all organophosphorus compounds | 3.4 | 1.5 | 1.3 |

|  | Field Organic I | Field Organic II | Field Organic III |
|---|---|---|---|
| (from $^{31}$P-NMR) |  |  |  |
| DTPA in heavy organic (product) sample as % of all organophosphorus compounds (from $^{31}$P-NMR) | 72 | 76 | 75 |

This example illustrates the ability of the method of invention to treat also nickel-containing Cyanex 301 organic solutions.

The extent of DTPA separation is also illustrated by the figures, showing typical $^{31}$P-NMR spectra for field organic, recovered DTPA organic and of the light organic phase. The peak at ~63 ppm represents DTPA, the peaks in the 76-80 ppm range represent recoverable disulfide compounds.

What is claimed is:

1. A method for recovering bis(2,4,4-trimethylpentyl) dithiophosphinic acid (DTPA) from a DTPA-containing organic solution, comprising:
   (a) contacting the DTPA-containing organic solution with an aqueous base solution supplied in excess of a stoichiometric requirement for acid-base neutralization or in excess of a stoichiometric requirement for metal cation-exchange reactions for the amount of DTPA contained in the organic solution to produce DTPA-rich and DTPA-lean organic phases;
   (b) separating the two organic phases;
   (c) contacting the DTPA-rich organic phase with a first acidic solution to produce a base-free DTPA-rich organic solution; and
   (d) contacting the DTPA-lean organic phase with a second acidic solution to produce a base-free DTPA-lean organic solution.

2. The method of claim 1, wherein the DTPA-containing organic solution contains organophosphorus compounds that have been produced from the oxidation of DTPA and are different from disulfide.

3. The method, of claim 1, wherein the step (a) is carried out at temperatures within the range between 25 and 70° C.

4. The method of claim 1, wherein the aqueous base solution of step (a) include aqueous solutions of alkali-metals hydroxides.

5. The method of claim 1, wherein the base solution of step (a) has a concentration greater than 1 mol/L.

6. The method of claim 1, wherein the base solution of step (a) includes 50 wt % sodium hydroxide or a 28 wt % ammonia solution.

7. The method of claim 1, wherein the separating of step (b) includes separating based on different specific densities.

8. The method of claim 1, wherein the DTPA-rich organic phase contains DTPA and its respective base salt, and the DTPA-lean organic phase comprises a hydrocarbon diluent containing an organophosphorus compound.

9. The method of claim 1, wherein a third phase comprising an aqueous base solution is formed in step (a).

10. The method of claim 1, wherein the DTPA-rich organic solution obtained in step (c) reusable for metal extraction operation.

11. The method of claim 1, wherein the base-free DTPA-lean organic solution obtained in step (d) is disposable or treatable for organic diluent recovery and reusable for metal extraction.

12. The method of claim 1, wherein the DTPA-rich organic solution obtained in step (c) is contacted with an acid aqueous solution in order to convert the base salt form of DTPA into the acid form of DTPA.

13. The method of claim 1, wherein the DTPA-rich organic solution obtained in step (c) is diluted to lower the DTPA concentration by using the DTPA-containing organic solution or an organic diluent used to prepare the DTPA-containing organic solution.

14. The method of claim 1, wherein the DTPA-lean organic phase is further treated by solvent distillation or steam stripping to separate and recover the majority of the hydrocarbon diluent from the higher boiling point organophosphorus compounds.

15. The method of claim 1, wherein the first acidic solution and the second acidic aqueous solution of steps (c) and (d) contain at least one mineral acid selected from the group consisting of hydrochloric and sulfuric acid.

16. The method of claim 2, wherein the DTPA-containing organic solution contains a base metal chemically bonded to DTPA.

17. The method of claim 16, wherein the base metal is selected from the group consisting of nickel, cobalt, zinc, copper and chromium.

18. The method of claim 3, wherein the step (a) is carried out at temperatures within the range between 45 and 55° C.

19. The method of claim 4, wherein the aqueous solutions of alkali-metals hydroxides are selected from the group consisting of sodium hydroxide, potassium hydroxide, and ammonium hydroxide.

20. The method of claim 5, wherein the base solution of step (a) has a concentration greater than 5 mol/L.

21. The method of claim 8, wherein the respective base salt is selected from the group consisting of sodium, potassium, and ammonium dithiophosphinate.

* * * * *